(12) United States Patent
Desjardin et al.

(10) Patent No.: US 11,751,907 B2
(45) Date of Patent: Sep. 12, 2023

(54) SURGICAL ACCESS DEVICE WITH SELF-INFLATING BALLOON

(71) Applicant: Covidien LP, Mansfield, MA (US)

(72) Inventors: Kevin M. Desjardin, Prospect, CT (US); Astley C. Lobo, West Haven, CT (US)

(73) Assignee: Covidien LP, Mansfield, MA (US)

( * ) Notice: Subject to any disclaimer, the term of this patent is extended or adjusted under 35 U.S.C. 154(b) by 326 days.

(21) Appl. No.: 17/229,243

(22) Filed: Apr. 13, 2021

(65) Prior Publication Data

US 2022/0323107 A1    Oct. 13, 2022

(51) Int. Cl.
*A61B 17/34* (2006.01)
*A61B 17/00* (2006.01)

(52) U.S. Cl.
CPC ...... *A61B 17/3439* (2013.01); *A61B 17/3423* (2013.01); *A61B 2017/00367* (2013.01); *A61B 2017/3441* (2013.01); *A61B 2017/3486* (2013.01)

(58) Field of Classification Search
None
See application file for complete search history.

(56) References Cited

U.S. PATENT DOCUMENTS

| 397,060 | A | 1/1889 | Knapp |
| 512,456 | A | 1/1894 | Sadikova |
| 1,213,005 | A | 1/1917 | Pillsbury |
| 2,912,981 | A | 11/1959 | Keough |
| 2,936,760 | A | 5/1960 | Gains |
| 3,039,468 | A | 6/1962 | Price |
| 3,050,066 | A | 8/1962 | Koehn |
| 3,253,594 | A | 5/1966 | Matthews et al. |
| 3,397,699 | A | 8/1968 | Kohl |
| 3,545,443 | A | 12/1970 | Ansari et al. |
| 3,713,447 | A | 1/1973 | Adair |
| 3,774,596 | A | 11/1973 | Cook |

(Continued)

FOREIGN PATENT DOCUMENTS

| EP | 0480653 A1 | 4/1992 |
| EP | 0610099 A2 | 8/1994 |

(Continued)

*Primary Examiner* — Jan Christopher L Merene
(74) *Attorney, Agent, or Firm* — Carter, DeLuca & Farrell LLP

(57) ABSTRACT

A surgical access device has a cannula tube with a collar coupled to a proximal region of the cannula tube. A balloon is attached to the cannula tube. The collar includes a receptacle and an inflater is insertable into the receptacle. The inflater has a body with a chamber and a first compound. A cap is attached to one end of the body and has a cavity containing a second compound. A membrane is disposed between the body and the cap and is configured to keep the first and second compounds separate. A button extends through an opening of the cap and a piston is coupled to the button. The piston includes a spike extending away from the button and is translatable in the cap between a rest position and an actuated position. The actuated position is defined by a portion of the spike penetrating the membrane such that the first compound interacts with the second compound generating a gas that is communicated to the balloon via a groove of the cannula tube.

20 Claims, 10 Drawing Sheets

(56) References Cited

U.S. PATENT DOCUMENTS

| | | |
|---|---|---|
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Fleischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,781,645 A * | 11/1988 | Kato .................. A63H 33/00 446/221 |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Mlgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Amey |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,893,866 A | 4/1999 | Hermann et al. |
| 5,925,058 A | 7/1999 | Smith et al. |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,447,529 B2 | 9/2002 | Fogarty et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 | 9/2004 | Cioanta et al. |
| 7,300,448 B2 | 11/2007 | Criscuolo et al. |
| 7,691,089 B2 | 4/2010 | Gresham |
| 8,454,645 B2 | 6/2013 | Criscuolo et al. |
| 8,926,508 B2 | 1/2015 | Hotter |
| 9,975,683 B2 * | 5/2018 | Davis .................. B65D 81/32 |
| 10,022,149 B2 | 7/2018 | Holsten et al. |

(56) References Cited

U.S. PATENT DOCUMENTS

| | | | | |
|---|---|---|---|---|
| 2007/0280042 A1* | 12/2007 | Yamanaka | ......... | B65D 51/2835 |
| | | | | 366/185 |
| 2018/0271557 A1* | 9/2018 | Buyda | ................ | A61B 17/3423 |
| 2019/0059937 A1* | 2/2019 | Buyda | ................ | A61B 17/3423 |
| 2020/0085612 A1* | 3/2020 | Clarke | ....................... | A61F 5/41 |
| 2021/0378705 A1* | 12/2021 | Desjardin | .......... | A61B 17/3423 |
| 2023/0088737 A1* | 3/2023 | Imran | .................. | A61M 5/155 |
| | | | | 604/891.1 |

FOREIGN PATENT DOCUMENTS

| | | |
|---|---|---|
| EP | 0880939 A1 | 12/1998 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |
| WO | 2016186905 A1 | 11/2016 |

* cited by examiner

SURGICAL ACCESS DEVICE WITH SELF-INFLATING BALLOON

FIELD

The present disclosure generally relates to a surgical access device. In particular, the present disclosure relates to a surgical access device having a self-inflating balloon.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula or an access port) is introduced through an opening in tissue (e.g., a naturally occurring orifice or an incision) to provide access to an underlying surgical site in the body. The opening is typically made using an obturator having a blunt or sharp tip that may be inserted through a passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instruments through the surgical access device to perform the minimally invasive surgical procedure.

Minimally invasive surgical procedures, including both endoscopic and laparoscopic procedures, permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through a cannula into the abdominal cavity to perform one or more surgical tasks. The cannula may incorporate a seal to establish a substantially fluid tight seal about the laparoscopic instrument to preserve the integrity of the pneumoperitoneum. The cannula, which is subjected to the pressurized environment, e.g., the pneumoperitoneum, may include an anchor to prevent the cannula from backing out of the opening in the abdominal wall, for example, during withdrawal of the laparoscopic instrument from the cannula.

SUMMARY

A surgical access device according to the present disclosure has a cannula tube with a collar coupled to a proximal region of the cannula tube. The collar includes a receptacle. A balloon is attached to the cannula tube and an inflater is insertable into the receptacle. The inflater includes a body having a chamber containing a first compound, a cap attached to one end of the body with a cavity containing a second compound, and a membrane disposed between the body and the cap. The membrane is configured to keep the first and second compounds separate. A button extends through an opening of the cap and a piston is coupled to the button. The piston includes a spike extending away from the button. The piston is translatable in the cap between a rest position and an actuated position. The actuated position is defined by a portion of the spike penetrating the membrane such that the first compound interacts with the second compound generating a gas that is communicated to the expandable balloon via a groove of the cannula tube.

In an aspect of the present disclosure, the inflater may further include a spring configured to bias the piston towards the rest position.

In aspects of the present disclosure, the surgical access device may further include an O-ring disposed between the button and the cap.

In yet another aspect of the present disclosure, the surgical access device may further include a filter attached to a distal end of the body and the filter is configured to block the flow of particulate matter.

In a further aspect of the present disclosure, the receptacle may include an orifice extending through an outer wall thereof.

In aspects of the present disclosure, the inflater may be threadably coupled with the receptacle such that in a first orientation the orifice is covered by a portion of the body and rotation of the inflater to a second orientation uncovers the orifice.

In another aspect of the present disclosure, the first compound may be baking soda, the second compound may be citric acid, and the gas may be carbon dioxide.

A surgical access device according to another aspect of the present disclosure includes a cannula tube with a balloon coupled to the cannula tube. The balloon has an expandable portion located in a distal region of the balloon. A collar is disposed in a proximal region of the cannula tube and includes a receptacle. An inflater has a body with a first end that is insertable into the receptacle and contains a first compound. A cap is attached to a second end of the body and contains a second compound. A membrane is disposed between the body and the cap. A button has a portion thereof extending through an opening of the cap. A piston having a spike is coupled to the button and translatable along a longitudinal axis of the inflater. The piston is translatable between a rest position and an actuated position. The actuated position is defined by the spike piercing the membrane allowing the first and second compounds to react and generate a gas that is communicated to the expandable portion of the balloon.

In aspects of the present disclosure, the cannula tube may include a groove in an outer surface thereof that fluidly couples the expandable portion of the balloon and the collar.

In an aspect of the present disclosure, the first compound may be baking soda and the second compound may be citric acid.

In a further aspect of the present disclosure, the first compound and the second compound may react to produce carbon dioxide gas.

In yet another aspect of the present disclosure, the surgical access device may further include a spring disposed between the body and the cap. The spring may be configured to bias the piston towards the rest position.

In aspects of the present disclosure, the surgical access device may further include a filter coupled to the first end of the body and the filter may be configured to block the flow of particulate matter.

In yet another aspect of the present disclosure, the receptacle may include an orifice extending through an outer wall thereof.

In another aspect of the present disclosure, the inflater may be threadably coupled with the receptacle such that in a first orientation the orifice is covered by a portion of the body and rotation of the inflater to a second orientation uncovers the orifice.

A method of expanding a balloon of a surgical access device according to an aspect of the present disclosure includes actuating a button of an inflater. The inflater is disposed in a receptacle of a collar that is coupled to a cannula tube. The method also includes piercing a membrane with a spike of a piston slidably positioned in a cap of the inflater where the membrane is disposed between a body of the inflater and the cap. Additionally, the method includes reacting a first compound disposed in the body with a second compound disposed in the cap and generating a gas. The method further includes expanding the balloon by communicating the gas from the inflater to the balloon via a groove in the cannula tube.

In aspects of the present disclosure, the surgical access device may include a spring disposed between the body and the cap. The spring may be configured to bias the piston towards a rest position. Actuating the button may include overcoming the bias of the spring.

In another aspect of the present disclosure, the first compound may be baking soda and the second compound may be citric acid. Reacting the first compound with the second compound may generate carbon dioxide gas.

In a further aspect of the present disclosure, the method may further include filtering particulate matter from the gas prior to expanding the balloon.

In yet another aspect of the present disclosure, the receptacle may have an orifice extending through an outer wall thereof and the inflater may be threadably coupled to the receptacle. The method may further include rotating the inflater between a first orientation in which the orifice is covered by a portion of the body and a second orientation in which the orifice is uncovered.

DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Figure 1:
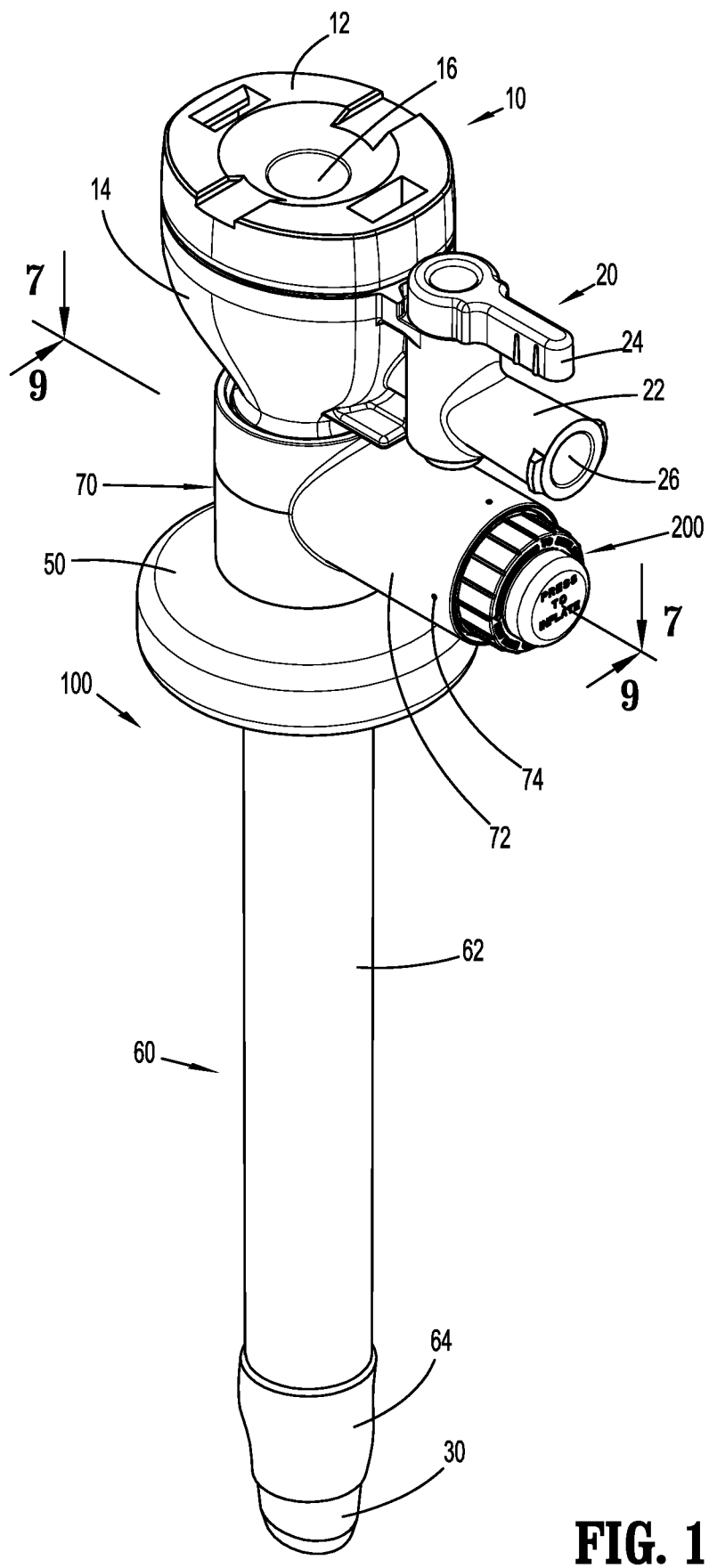
FIG. 1 is a perspective view of a surgical access device including a balloon according to an aspect of the present disclosure.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Descriptions of technical features of an aspect of the disclosure should typically be considered as available and applicable to other similar features of another aspect of the disclosure. Accordingly, technical features described herein according to one aspect of the disclosure may be applicable to other aspects of the disclosure, and thus duplicative descriptions may be omitted herein. Like reference numerals may refer to like elements throughout the specification and drawings. For a detailed description of the structure and function of exemplary surgical access assemblies, reference may be made to U.S. Pat. Nos. 7,300,448; 7,691,089; and 8,926,508, the entire content of each of which is hereby incorporated by reference herein.

Figure 9:
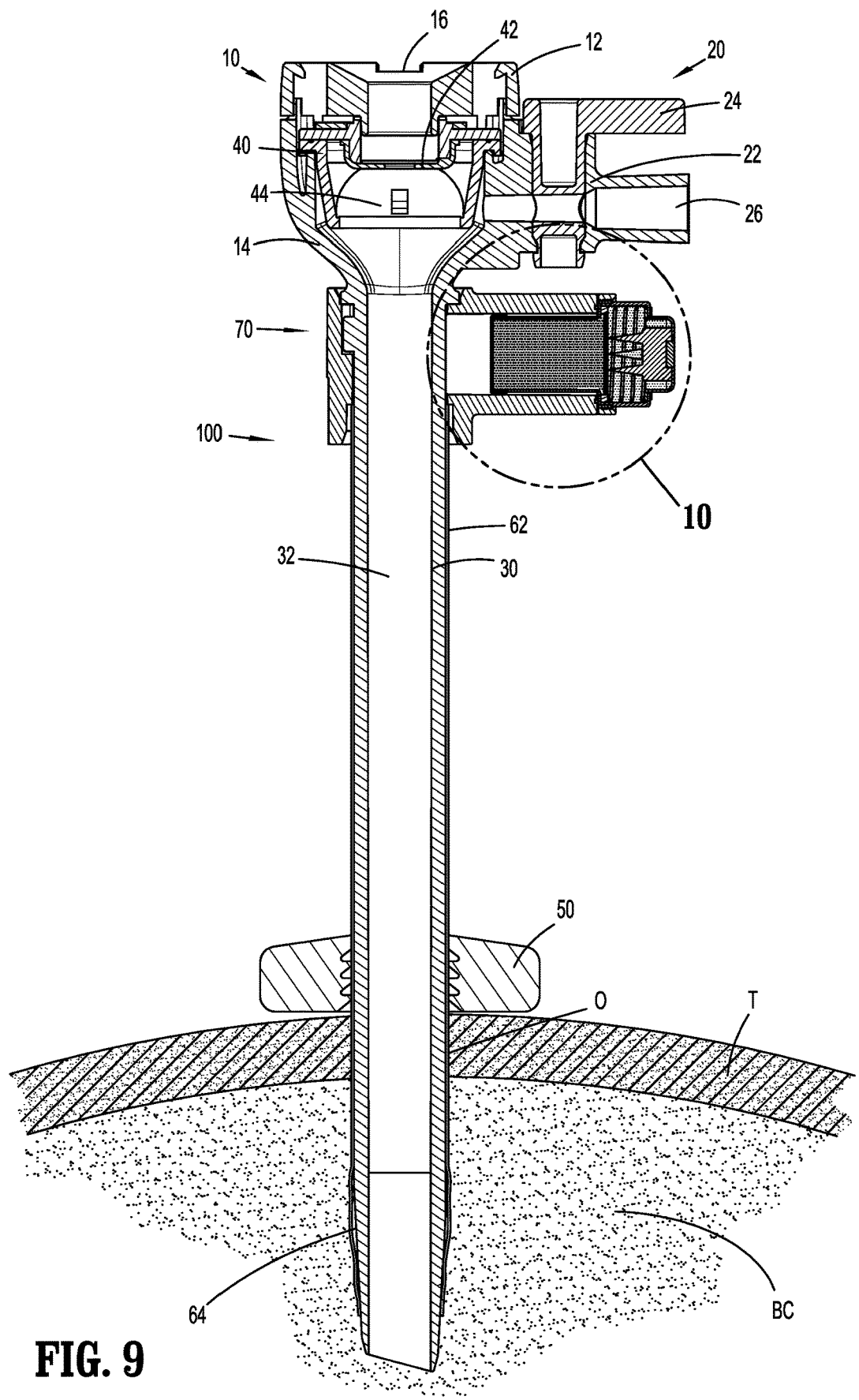
FIG. 9 is a side cross-sectional view of the surgical access device of FIG. 1 taken along section line 9-9 and the surgical access device being positioned through tissue.
Figure 11:
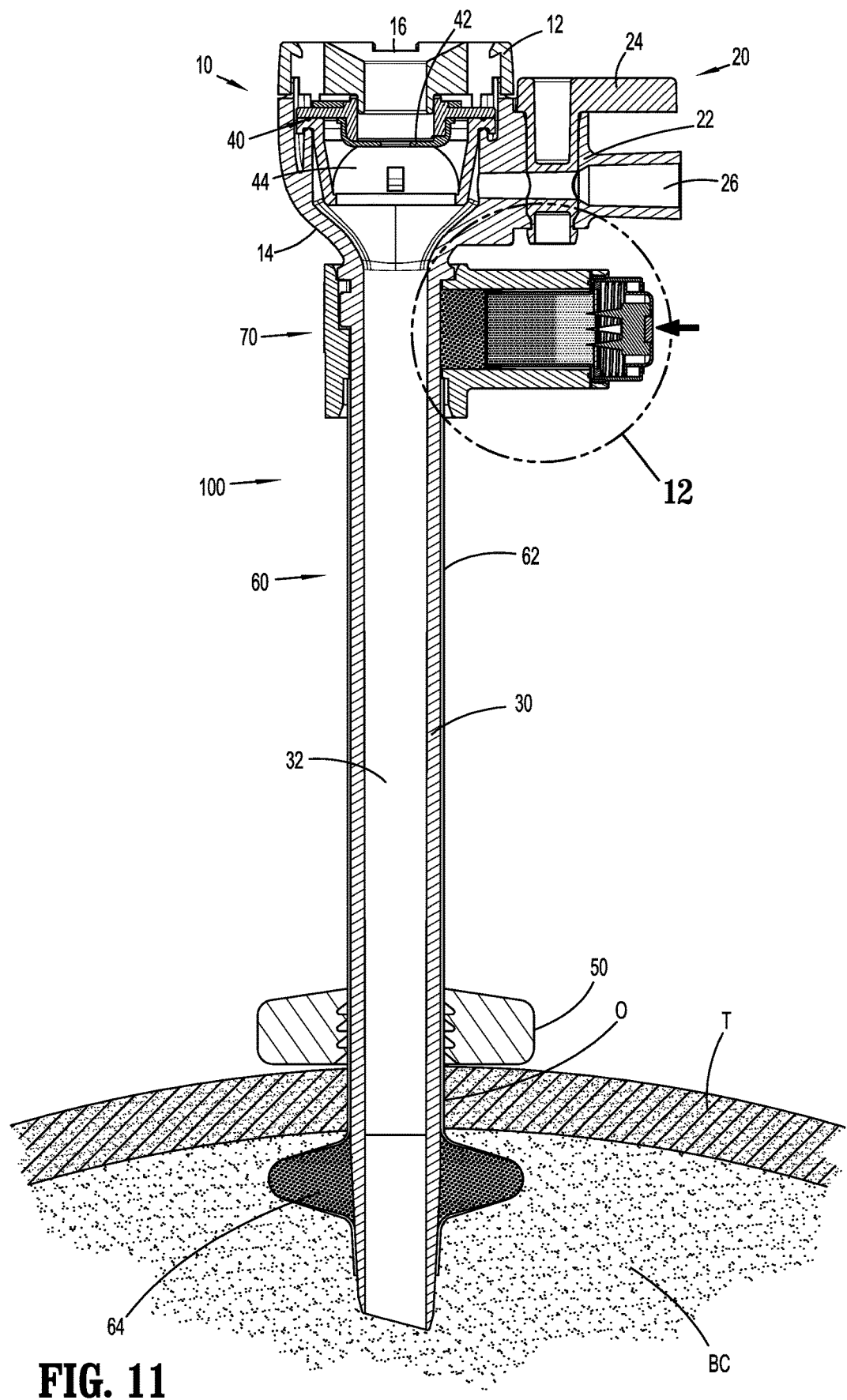
FIG. 11 is a side cross-sectional view of the surgical access device of FIG. 9 with the inflater actuated and an expandable portion of the balloon in an inflated condition.
Figure 12:
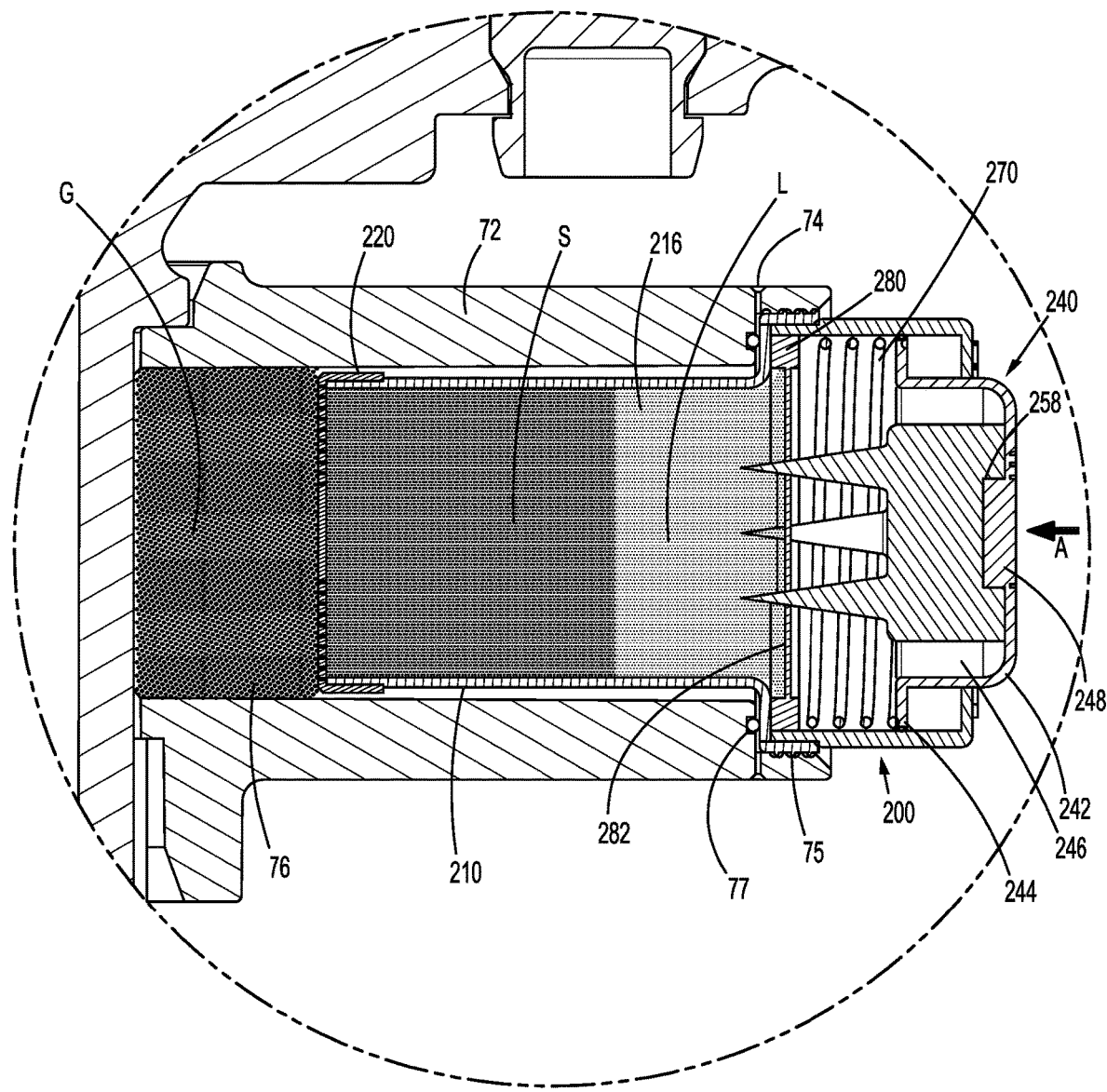
FIG. 12 is an enlarged view of the area of detail of FIG. 11 illustrating the inflater in an actuated position.
Figure 13:
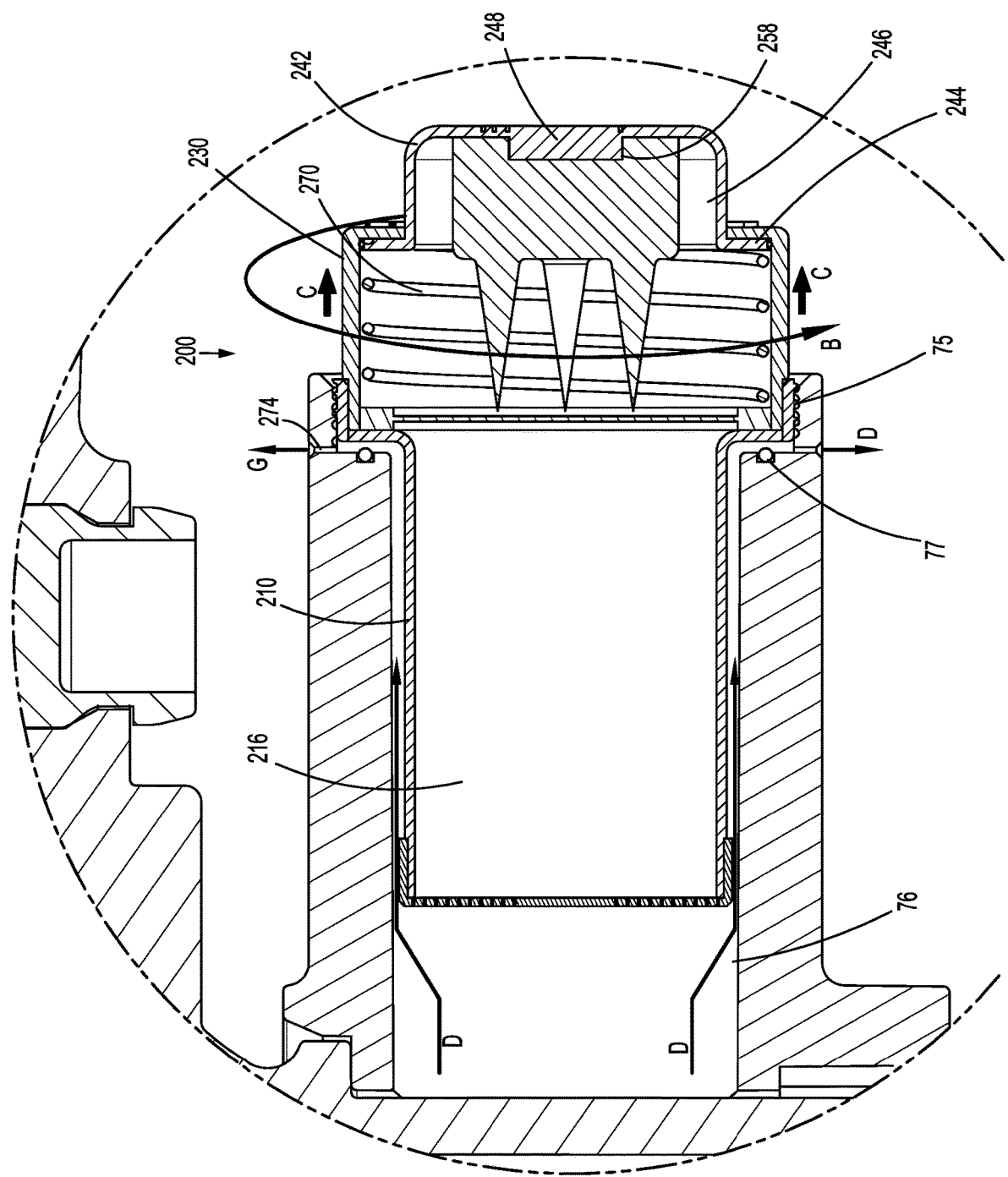
FIG. 13 is the area of detail shown in FIG. 12 illustrating rotation of the inflater from a first orientation to a second orientation.

Initially, with reference to FIGS. 1 and 9, a surgical access device 100 is illustrated. The surgical access device 100 has a housing 10 with an upper portion 12 and a lower portion 14. The upper portion 12 may be separable from the lower portion 14. A tubular member or cannula tube 30 extends from the lower portion 14 of the housing 10. The housing 10 and the cannula tube 30 are formed from a suitable biocompatible polymeric material (e.g., polycarbonate). The cannula tube 30 includes a lumen 32 that is configured to receive a surgical instrument, such as an obturator, endoscopic stapler, an electrosurgical instrument, etc., (not shown) therein. The lumen 32 of the cannula tube 30 is coaxial with a proximal opening 16 of the housing 10. Additionally, the lower portion 14 of the housing 10 has a valve 20 extending radially therefrom. The valve 20 includes a body 22, a handle 24, and a valve port 26. The handle 24 is rotatable relative to the body 22 such that a first position of the handle 24 defines an open configuration of the valve 20 that allows fluid to flow through the valve 20 and a second position of the handle 24 defines a closed configuration of the valve 20 that inhibits fluid from flowing through the valve 20. The valve 20 may be a stop cock valve. A seal assembly 40 is disposed in the housing 10. The seal assembly 40 includes an instrument seal 42 that is configured to sealing engage a surgical instrument (not shown) inserted through an opening of the instrument seal 42. Additionally, the seal assembly 40 includes an instrument valve 44 disposed distally of the instrument seal 42. The instrument valve 44 is a conical elastomeric membrane, such as a duckbill or zero-closure valve fabricated from a resilient material, such as, for example, rubber, etc. The instrument valve 44 is flexible for resilient reception of a surgical instrument therethrough. The instrument valve 44 forms a substantial seal with a shaft of a surgical instrument inserted therethrough. In the absence of a surgical instrument, the instrument valve 44 forms a fluid tight seal between the lumen 32 of the cannula tube 30 and the upper portion 12 of the housing 10. A skin seal 50 is slidably mounted on an outer surface of the cannula tube 30 and is repositionable along the cannula tube 30 to increase stability of the surgical access device 100 when it is positioned through an opening O in body tissue T. The skin seal 50 may be a foam collar. The skin seal 50 is also slidable along an outer surface of a sleeve 62 of a balloon 60. The balloon 60 includes the sleeve 62 extending along the cannula tube 30 and an expandable portion 64 located in a distal region of the balloon 60 which corresponds to a distal region of the cannula tube 30. The expandable portion 64 of the balloon 60 is transitionable between an initial or collapsed configuration (FIG. 9) and an inflated or expanded configuration (FIG. 11). The sleeve 62 of the balloon 60 is attached to the cannula tube 30 using adhesives or ultrasonic welding. Additionally, regions of the balloon 60 that are located proximally and distally of the expandable portion 64 are also attached to the cannula tube 30 using adhesives or ultrasonic welding.

Figure 3:
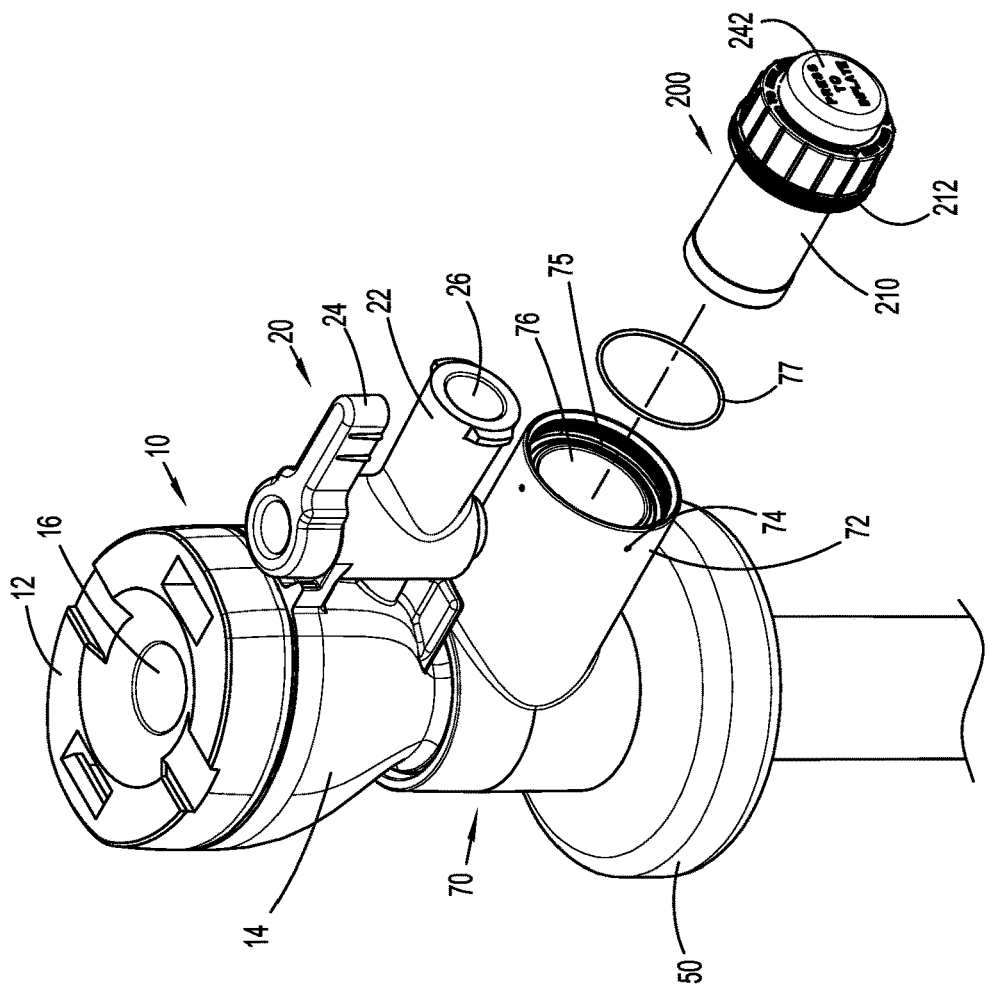
FIG. 3 is a perspective view of a proximal portion of the surgical access device of FIG. 1 with the inflater separated from the collar of the surgical access device.
Figure 2:
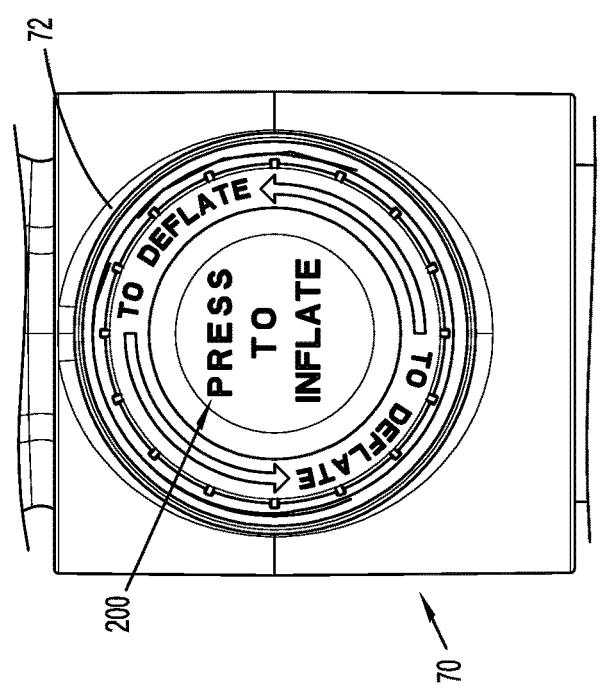
FIG. 2 is an end view of an inflater coupled to a collar of the surgical access device of FIG. 1.

Referring now to FIGS. 1-3, the surgical access device 100 further includes a collar 70 that circumscribes the cannula tube 30 and is positioned in a proximal region of the cannula tube 30 near the lower portion 14 of the housing 10. The collar 70 has a radially extending receptacle 72 with an open end. The open end of the receptacle 72 provides access to a compartment 76. The receptacle 72 has orifices 74 extending through an outer wall of the receptacle 72. The orifices 74 provide fluid communication between the receptacle 72 and the ambient air surrounding the surgical access device 100. An inflation assembly or inflater 200 is insertable into the compartment 76 of the receptacle 72. Specifically, the inflater 200 has a body 210 that is insertable into the compartment 76. An O-ring 77 is positioned in the open end of the receptacle 72 and surrounds the body 210 of the inflater 200 when the inflater 200 is seated in the compartment 76 of the receptacle 72. The O-ring 77 provides a fluid-tight boundary where the inflater 200 is attached to receptacle 72. The inflater 200 also has a filter 220 disposed on a distal end of the body 210 and a cap 230 attached to a proximal end of the body 210. The body 210 includes threads 212 that complement threads 75 of the receptacle 72 for retaining the inflater 200 within the receptacle 72. This threaded arrangement between the receptacle 72 and the body 210 of the inflater 200 allows the inflater 200 to be screwed into the receptacle 72 by rotating the inflater 200 in a first direction relative to the receptacle 72. Rotating the inflater 200 in a second and opposite direction relative to the receptacle 72 unscrews the inflater 200 from the receptacle 72. The inflater 200 may also be partially unscrewed from the receptacle 72 as will be discussed in detail hereinbelow. A button is disposed in the inflater 200 and a portion of the button is accessible through an opening 232 of the cap 230.

Figure 6:
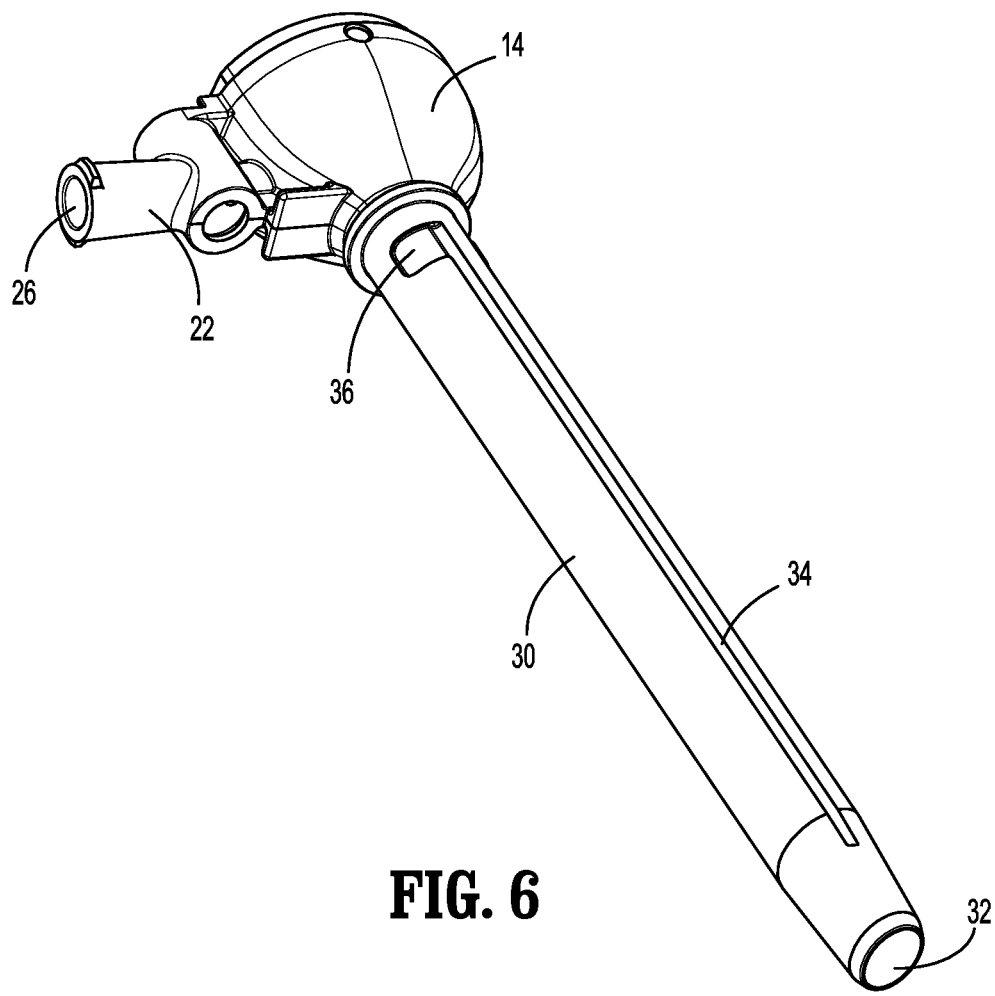
FIG. 6 is a perspective view of the surgical access device of FIG. 1 with the balloon removed illustrating a groove in an outer wall of a cannula tube.
Figures 7, 8:
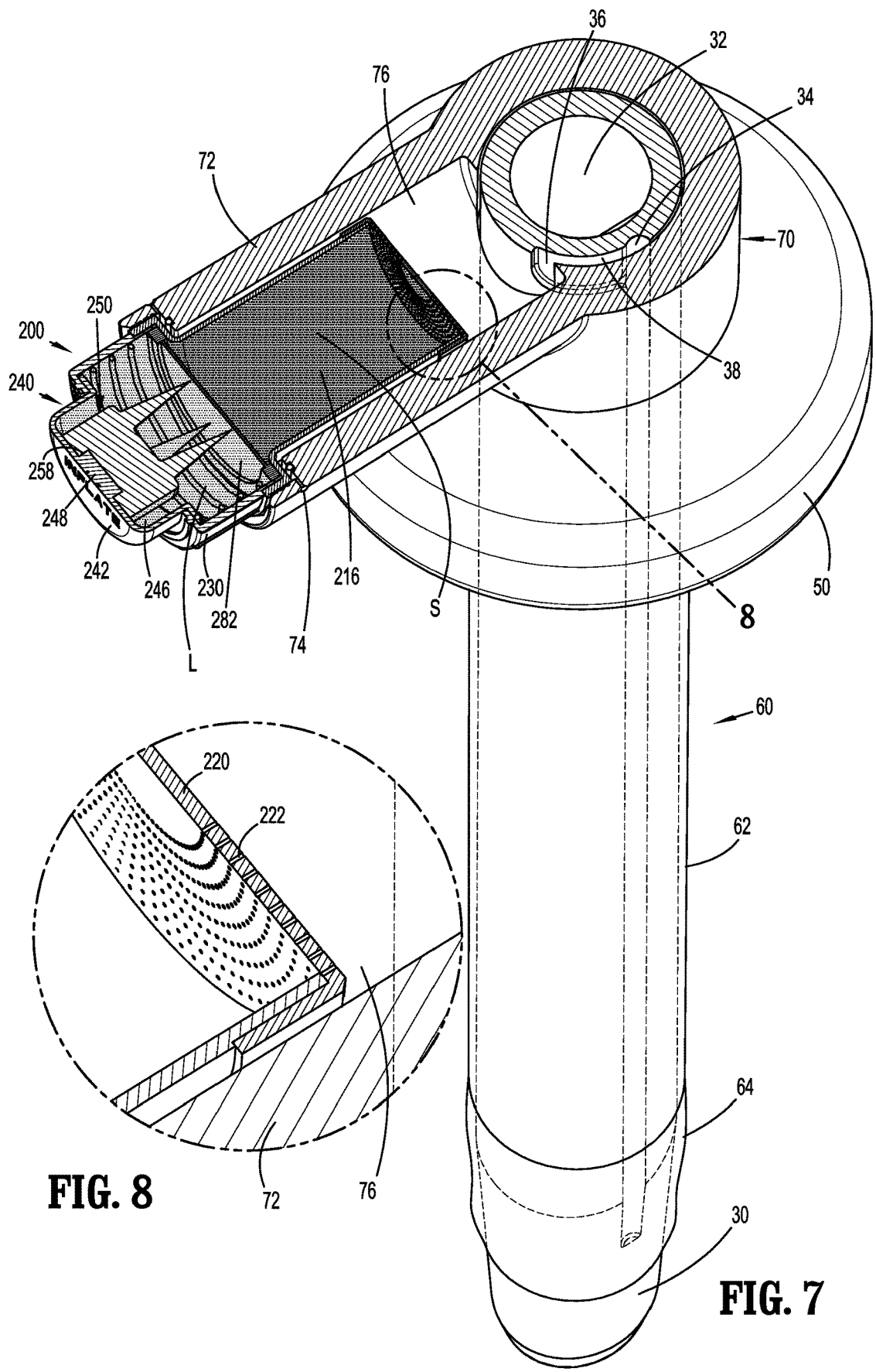
FIG. 7 is a top cross-sectional view of the surgical access device of FIG. 1 taken along section line 7-7 illustrating aspects of the inflater.
FIG. 8 is an enlarged view of the area of detail of FIG. 7 illustrating aspects of a filter of the inflater.

Briefly referring to FIG. 6, the surgical access device 100 is shown with the balloon 60 and the collar 70 removed. A groove 34 extends along a majority of a length of the cannula tube 30. A radially extending pocket 36 is located in a proximal region of the groove 34. Both the groove 34 and the pocket 36 extend into an outer wall of the cannula tube 30 and are in fluid communication with one another. As shown in FIG. 7, the receptacle 72 of the collar 70 is in fluid communication with the pocket 36 and thus the groove 34. Specifically, an inner surface of the collar 70 is spaced from the pocket 36 defining a channel 38 allowing fluid transfer between the receptacle 72 and the groove 34. A distal portion of the groove 34 is in fluid communication with the expandable portion 64 of the balloon 60. This arrangement allows fluid communication between the inflater 200 and the expandable portion 64 of the balloon 60.

Figure 4:
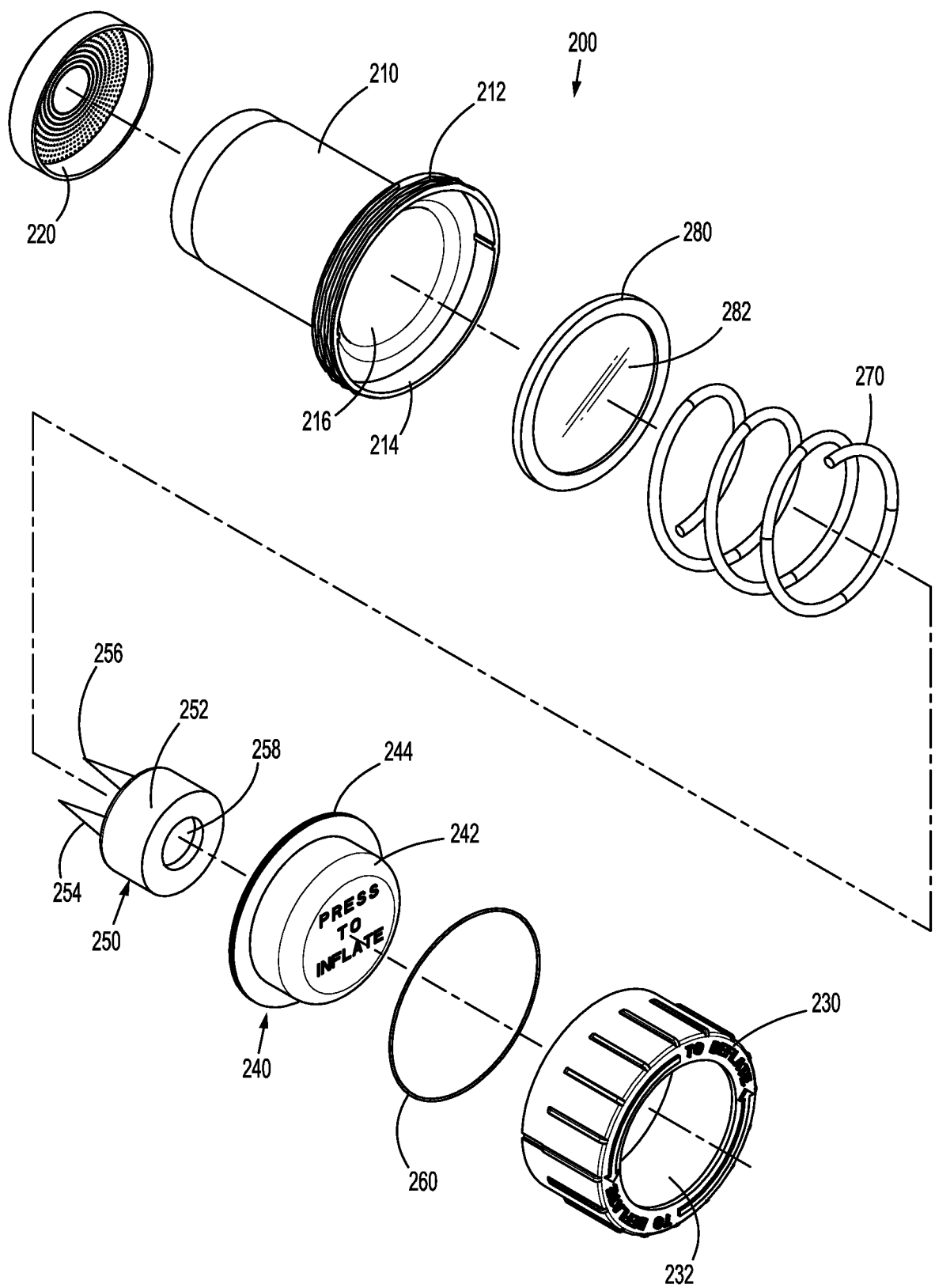
FIG. 4 is an exploded perspective view, with parts separated, of the inflater of FIG. 3.

Turning now to FIGS. 4 and 8, details of the inflater 200 are shown. The body 210 of the inflater 200 has a generally cylindrical configuration with open proximal and distal ends. The filter 220 is disposed at the distal end of the body 210 and covers the open distal end of the body 210. The threads 212 are located at the proximal end of the body 210 and have an outer diameter greater than the outer diameter of the body 210. The threads 212 surround the open proximal end of the body 210. A chamber 216 is defined between the proximal and distal ends and is configured to store a quantity of a first substance S (FIG. 7). The larger diameter threads 212 define a recess 214 with a shoulder at the proximal end that is configured to receive a disc 280 with a membrane 282 attached to the disc 280. The disc 280 rests in the recess 214 and the membrane 282 covers the open proximal end of the body 210. The membrane 282 is attached to the disc 280 such that it covers an opening in a center of the disc 280. The disc 280 is maintained in the recess 214 by friction. As assembled, the membrane 282 covers the open proximal end of the body 210 and the filter 220 covers the open distal end of the body 210. The filter 220 is a cap with an inner diameter slightly greater than the outer diameter of the body 210 such that, when attached to the body 210, the filter 220 is frictionally retained on the body 210. Alternatively, the filter 220 may be ultrasonically welded to the body 210. The filter 220 has pores 222 that permit the passage of gaseous material while blocking the passage of particulate material. As such, particulate material stored in the chamber 216 of the body 210 is retained within the chamber 216 of the body 210 between the filter 220 and the membrane 282. It is contemplated that the filter 220 may be formed from flashspun high-density polyethylene fibers such as TYVEK®. The particulate material or first substance S disposed in the chamber 216 of the body 210 is sodium bicarbonate or baking soda ($NaHCO_3$). It is contemplated that potassium bicarbonate ($KHCO_3$) or sodium carbonate ($Na_2CO_3$) may be substituted for sodium bicarbonate.

Figure 5:
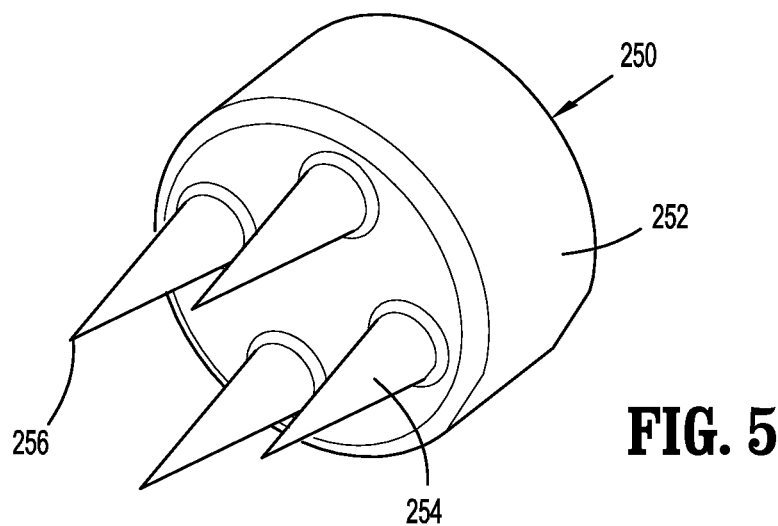
FIG. 5 is a bottom perspective view of a piston of the inflater of FIG. 4.
Figure 10:
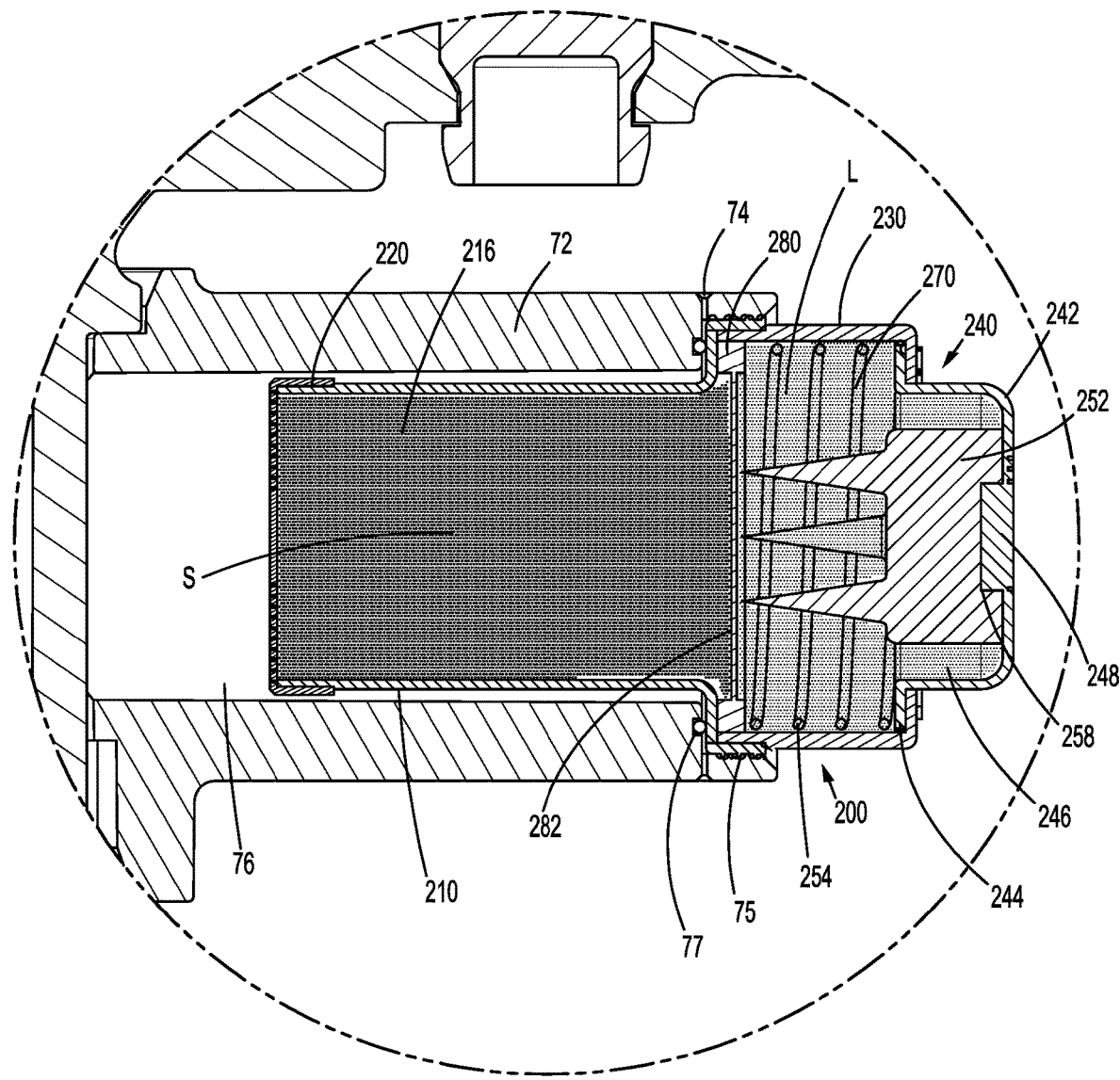
FIG. 10 is an enlarged view of the area of detail of FIG. 9 illustrating the inflater in a rest position.

With additional reference to FIGS. 5, 7, and 10, the cap 230 is partially inserted into the recess 214 of the body 210 and ultrasonically welded in place. The cap 230 has opposed proximal and distal openings defining a cavity 232 therebetween. The distal opening of the cap 230 is adjacent to the disc 280 and the membrane 282 while a proximal portion 242 of the button 240 extends through the proximal opening of the cap 230 and is readily accessible by a user. An O-ring 260 is positioned between the cap 230 and a flange 244 of the button 240 and provides a fluid-tight boundary where the flange 244 of the button 240 engages an inner surface of the cap 230. The button 240 includes a dome 246 that is surrounded by the flange 244 and is configured to receive a portion of a piston 250 therein. The piston 250 has a cylinder 252 with spikes 254 extending therefrom. As illustrated, the piston 250 includes four spikes 254. However, the piston 250 may include more than four spikes 254 or less than four spikes 254. The cylinder 252 is partially disposed in the dome 246 of the button 240 and is retained within the dome 246 via a friction fit. In particular, the cylinder 252 has a depression 258 that mates with a protrusion 248 in the dome 246 of the button 240 thereby providing a friction fit between the piston 250 and the button 250. Each spike 254 has a piercing tip 256 adapted to pierce through the membrane 282. A biasing member 270, such as a spring, is disposed between the disc 280 and the flange 244 of the button 240. As shown, the biasing member 270 is a coil spring. The spring 270 biases the button 240 and the piston 250 towards a rest position. In the rest position, the proximal portion 242 of the button 240 is fully extended through the opening of the cap 230 and the piercing tips 256 of the spikes 254 are spaced from the membrane 282 of the disc 280. By positioning the disc 280 and membrane 282 between the body 210 and the cap 230, a second substance L disposed in the cavity 232 of the cap 230 is retained therein. The second substance L disposed in the cavity 232 of the cap 230 is liquid citric acid ($C_6H_8O_7$). It is contemplated that acetic acid ($C_2H_4O_2$) may be substituted for citric acid.

Referring briefly to FIG. 4, the inflater 200 may be assembled by inserting the disc 280 with the membrane 282 in the recess 214 of the body 210 such that the disc 280 is frictionally retained in the recess 214. The first substance S is added to the chamber 216 of the body 210 and the filter 220 is installed over the distal end of the body 210. Alternatively, the filter 220 may be attached first with the disc 280 being attached after the first substance S is added to the chamber 216. The filter 220 and the disc 280 may be ultrasonically welded to the body 210. The O-ring 260 is placed into the cap 230 followed by the button 240 such that the proximal portion 242 of the button 240 extends through the opening of the cap 230. The piston 250 is coupled to the button 240 by the interference fit between the depression 258 of the piston 250 and the protrusion 248 of the button 246. The piston 250 may be coupled to the button 240 before or after the button 240 is attached to the cap 230. The spring 270 is placed in the cavity 232 of the cap 230 and the liquid substance L is added to the cavity 232. Subsequently, the cap 230 is attached to the body 210 and ultrasonically welded in place. Alternatively, the cap 230 may be press fit into the body 210 of the inflater 200. As assembled, the spring 270 biases the button 240 and the piston 250 towards the rest position which defines a gap between the spikes 254 and the membrane 282 of the disc 280. As mentioned above, the membrane 282 of the disc 280 provides a boundary separating the first substance S in the chamber 216 of the body 210 and the second substance L in the cavity 232 of the cap 230.

With reference now to FIGS. 9-13, operation and use of the surgical access device 100 is depicted. As seen in FIG. 9, the surgical access device 100 allows access to a surgical site (i.e., a body cavity) BC beneath body tissue T (i.e., skin) via the lumen 32 of the cannula tube 30. The surgical access device 100 is inserted through an opening O in body tissue T with the expandable portion 64 of the balloon 60 in the initial configuration. This facilitates inserting the cannula tube 30 of the surgical access device 100 through the opening O in body tissue T. Once the surgical access device 100 is placed in a desired position by the clinician, the skin seal 50 is slid distally until a distal surface of the skin seal 50 contacts an outer surface of body tissue T. Additionally, the button 240 and piston 250 are in the rest position which maintains the first substance S separate from the second substance L. The inflater 200 is fully seated within the receptacle 72 such that a portion of the body 210 of the inflater 200 covers the orifices 74 of the receptacle 72 preventing fluid flow between the receptacle 72 and the atmosphere surrounding the surgical access device 100. Subsequently, the clinician depresses the button 240 in the direction of arrow "A" which overcomes the bias of the spring 270 and translates the piston 250 towards the membrane 282 of the disc 280. The piercing tips 256 of the spikes 254 penetrate the membrane 282 allowing the first substance S to mix with the second substance L. When the first substance S, sodium bicarbonate, reacts with the second substance L, citric acid, the chemical reaction forms carbon dioxide gas G ($CO_2$), water ($H_2O$), and sodium citrate ($Na_3C_6H_5O_7$) as the byproducts. The balanced equation is $C_6H_8O_7 + 3NaHCO_3 \rightarrow Na_3C_6H_5O_7 + 3H_2O + 3CO_2$. The quantities of the sodium bicarbonate and citric acid are selected such that the reaction will produce a desired amount of carbon dioxide gas G. The quantities chose may or may not result in complete consumption of either substance as long as the desired amount of carbon dioxide gas G is produced. Although the bicarbonates and the acids are discloses as specific examples of the first and second compounds, any two compounds which generate a gas when mixed may be used as the first and second compounds. In aspects, the gas generated by reacting the first and second compounds may be carbon dioxide.

As the orifices 74 of the receptacle 72 are blocked by the body 210 of the inflater 200, the only available flow path for the carbon dioxide gas G is through the pores 222 of the filter 220, through the channel 38 defined between the pocket 36 and the inner surface of the collar 70, along the groove 34 in the cannula tube 30, and into the expandable portion 64 of the balloon 60. Since the carbon dioxide gas G has a pressure greater than a pressure outside the surgical access device 100, the expandable portion 64 of the balloon 60 transitions from the collapsed configuration (FIG. 9) to the expanded configuration (FIG. 11). The pores 222 of the filter 220 are sized to allow the carbon dioxide gas G to travel from the chamber 216 of the body 210 of the inflater 200 to the channel 38 defined between the inner surface of the collar 70 and the pocket 36 while keeping the particulate matter of the first substance S and solid by products of the chemical reaction within the chamber 216 of the body 210 of the inflater 200. With the expandable portion 64 of the balloon 60 in the expanded configuration and the skin seal 50 abutting the outer surface of body tissue T, the surgical access device 100 is anchored in the opening O and resists movement. When the clinician is ready to remove the surgical access device 100 from the patient, the clinician rotates the cap in the direction of arrow "B" such that the inflater 200 backs out of the receptacle 72 as indicated by arrows "C". By moving the body 210 slightly out of the receptacle 72 while still maintaining a threaded engagement between the inflater 200 and the receptacle 72, the orifices 74 of the receptacle 72 are no longer blocked by the body 210 and provide an exit path for the carbon dioxide gas G around the body of the inflater 200 as shown by arrows "D". This action deflates the expandable portion 64 of the balloon 60 such that it transitions from the expanded configuration to the collapsed configuration allowing the surgical access device 100 to be removed.

Persons skilled in the art will understand that the devices and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:
1. A surgical access device comprising:
   a cannula tube;
   a collar coupled to the cannula tube in a proximal region thereof, the collar including a receptacle;
   a balloon attached to the cannula tube; and
   an inflater insertable into the receptacle, the inflater including:
      a body having a chamber, the chamber containing a first compound,
      a cap attached to one end of the body, the cap having a cavity containing a second compound, a membrane disposed between the body and the cap, the membrane configured to keep the first and second compounds separate, a button extending through an opening of the cap, and a piston coupled to the button, the piston including a spike extending away from the button, the piston translatable in the cap between a rest position and an actuated position, the actuated position defined by a portion of the spike penetrating the membrane such that the first compound interacts with the second compound generating a gas that is communicated to the balloon via a groove of the cannula tube.

2. The surgical access device according to claim 1, wherein the inflater further includes a spring configured to bias the piston towards the rest position.

3. The surgical access device according to claim 1, further including an O-ring disposed between the button and the cap.

4. The surgical access device according to claim 1, further including a filter attached to a distal end of the body, the filter configured to block the flow of particulate matter.

5. The surgical access device according to claim 1, wherein the receptacle includes an orifice extending through an outer wall thereof.

6. The surgical access device according to claim 5, wherein the inflater is threadably coupled with the receptacle such that in a first orientation the orifice is covered by a portion of the body and rotation of the inflater to a second orientation uncovers the orifice.

7. The surgical access device according to claim 1, wherein the first compound is baking soda, the second compound is citric acid, and the gas is carbon dioxide.

8. A surgical access device comprising:
a cannula tube;
a balloon coupled to the cannula tube, the balloon having an expandable portion located in a distal region thereof;
a collar disposed in a proximal region of the cannula tube, the collar including a receptacle; and
an inflater having:
a body with a first end insertable into the receptacle, the body containing a first compound,
a cap attached to a second end of the body, the cap containing a second compound,
a membrane disposed between the body and the cap,
a button having a portion thereof extending through an opening of the cap, and
a piston having a spike, the piston coupled to the button and translatable along a longitudinal axis of the inflater, the piston translatable between a rest position and an actuated position, the actuated position defined by the spike piercing the membrane allowing the first and second compounds to react and generate a gas that is communicated to the expandable portion of the balloon.

9. The surgical access device according to claim 8, wherein the cannula tube includes a groove in an outer surface thereof, the groove fluidly coupling the expandable portion of the balloon and the collar.

10. The surgical access device according to claim 8, wherein the first compound is baking soda and the second compound is citric acid.

11. The surgical access device according to claim 10, wherein the first compound and the second compound react to produce carbon dioxide gas.

12. The surgical access device according to claim 8, further including a spring disposed between the body and the cap, the spring configured to bias the piston towards the rest position.

13. The surgical access device according to claim 8, further including a filter coupled to the first end of the body, the filter configured to block the flow of particulate matter.

14. The surgical access device according to claim 8, wherein the receptacle includes an orifice extending through an outer wall thereof.

15. The surgical access device according to claim 14, wherein the inflater is threadably coupled with the receptacle such that in a first orientation the orifice is covered by a portion of the body and rotation of the inflater to a second orientation uncovers the orifice.

16. A method of expanding a balloon of a surgical access device comprising:
actuating a button of an inflater, the inflater disposed in a receptacle of a collar that is coupled to a cannula tube;
piercing a membrane with a spike of a piston slidably positioned in a cap of the inflater, the membrane disposed between a body of the inflater and the cap;
reacting a first compound disposed in the body with a second compound disposed in the cap and generating a gas; and
expanding the balloon by communicating the gas from the inflater to the balloon via a groove in the cannula tube.

17. The method according to claim 16, wherein the surgical access device includes a spring disposed between the body and the cap, the spring configured to bias the piston towards a rest position, and actuating the button includes overcoming the bias of the spring.

18. The method according to claim 16, wherein the first compound is baking soda, the second compound is citric acid, and reacting the first compound with the second compound generates carbon dioxide gas.

19. The method according claim 16, further comprising filtering particulate matter from the gas prior to expanding the balloon.

20. The method according to claim 16, wherein the receptacle has an orifice extending through an outer wall thereof and the inflater is threadably coupled to the receptacle, the method further comprising rotating the inflater between a first orientation in which the orifice is covered by a portion of the body and a second orientation in which the orifice is uncovered.

* * * * *